US007943386B2

(12) United States Patent
Grumann et al.

(10) Patent No.: US 7,943,386 B2

(45) Date of Patent: May 17, 2011

(54) APPARATUS AND METHOD FOR DETERMINING THE VOLUME FRACTIONS OF THE PHASES IN A SUSPENSION

(75) Inventors: Markus Grumann, Muehlhelm (DE); Jens Ducrée, Freiburg (DE); Roland Zengerle, Waldkirch (DE); Lutz Riegger, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 412 days.

(21) Appl. No.: 12/067,226

(22) PCT Filed: Oct. 5, 2006

(86) PCT No.: PCT/EP2006/009660

§ 371 (c)(1),
(2), (4) Date: Apr. 18, 2008

(87) PCT Pub. No.: WO2007/042207

PCT Pub. Date: Apr. 19, 2007

(65) Prior Publication Data

US 2008/0280365 A1 Nov. 13, 2008

(30) Foreign Application Priority Data

Oct. 7, 2005 (DE) ......................... 10 2005 048 236

(51) Int. Cl.
*G01N 33/86* (2006.01)
*G01N 33/48* (2006.01)
*G01N 1/18* (2006.01)

(52) U.S. Cl. ................ 436/70; 436/43; 436/45; 436/63; 436/174; 436/177; 436/180; 422/64; 422/72; 422/73; 422/527; 422/533; 73/61.68

(58) Field of Classification Search .................... 436/43, 436/45, 63, 70, 174, 177, 180; 422/63, 64, 422/68.1, 72, 73, 100, 101, 527, 533; 73/61.65, 61.68
See application file for complete search history.

(56) References Cited

U.S. PATENT DOCUMENTS 3,009,388 A 11/1961 Polanyi
(Continued)

FOREIGN PATENT DOCUMENTS

DE 103 25 110 B3 1/2005
(Continued)

OTHER PUBLICATIONS

Official communication issued in counterpart International Application No. PCT/EP2006/009660, mailed on May 8, 2008.

(Continued)

*Primary Examiner* — Maureen M Wallenhorst
(74) *Attorney, Agent, or Firm* — Keating & Bennett, LLP

(57) ABSTRACT

An apparatus for determining the volume fractions of the phases in a suspension includes a body, a channel structure, which is formed in the body, and an inlet area and a blind channel, which is fluidically connected to and capable of being filled via the same. Furthermore, a drive for imparting the body with rotation, so that phase separation of the suspension in the blind channel takes place, is provided. The blind channel includes such a channel cross-section and/or such wetting properties that, when filling same via the inlet area, higher capillary forces act in a first cross-sectional area than in a second cross-sectional area, so that at first the first cross-sectional area fills in the direction from the inlet area toward the blind end of the blind channel and then the second cross-sectional area fills in the direction from the blind end toward the inlet area.

15 Claims, 7 Drawing Sheets

U.S. PATENT DOCUMENTS

| | | | | |
|---|---|---|---|---|
| 4,052,164 | A | 10/1977 | König | |
| 4,055,076 | A | 10/1977 | Tropea | |
| 4,740,472 | A | 4/1988 | Burtis et al. | |
| 4,742,718 | A | 5/1988 | Jimbo | |
| 4,761,381 | A | 8/1988 | Blatt et al. | |
| 4,963,326 | A | 10/1990 | Eberle | |
| 5,061,381 | A * | 10/1991 | Burd | 210/789 |
| 5,242,606 | A * | 9/1993 | Braynin et al. | 210/787 |
| 5,279,150 | A | 1/1994 | Katzer et al. | |
| 5,316,952 | A * | 5/1994 | Brimhall | 436/70 |
| 5,594,164 | A * | 1/1997 | Bull | 73/61.66 |
| 6,319,469 | B1 * | 11/2001 | Mian et al. | 422/64 |
| 6,319,719 | B1 * | 11/2001 | Bhullar et al. | 436/70 |
| 6,406,672 | B1 * | 6/2002 | Bhullar et al. | 422/101 |
| 7,094,354 | B2 * | 8/2006 | Pugia et al. | 210/787 |

FOREIGN PATENT DOCUMENTS

| | | | |
|---|---|---|---|
| EP | 0 392 475 | A2 | 10/1990 |
| JP | 8-220088 | A | 8/1996 |
| JP | 2004-340758 | A | 12/2004 |
| WO | 94/18557 | A1 | 8/1994 |
| WO | 98/39645 | A1 | 9/1998 |
| WO | 99/41147 | A1 | 8/1999 |
| WO | 00/53321 | A1 | 9/2000 |
| WO | 2004/061413 | A2 | 7/2004 |

OTHER PUBLICATIONS

Official communication issued in the International Application No. PCT/EP2006/009660 mailed on Jan. 30, 2007.

Thomas, "Labor und Diagnose", pp. 492-495.

Dorner: "Klinische Chemie und Hamatologie," Georg Thieme Verlag; Germany; 1998; pp. 152-153.

Goldschmidtboeing et al.: "Strategies for Void-Free Liquid-Filling of Micro Cavitites," Proceedings of Transducers '05 Conference; Jun. 5-9, 2005; pp. 1561-1564.

Steinert et al.: "Bubble-Free Priming of Blind Channels," Proceedings of IEEE-MEMS; Jan. 25-29, 2004; pp. 224-228.

Kohnle et al.: "A Unique Solution for Preventing Clogging of Flow Channels by Gas Bubbles," Technical Digest IEEE Micro Electro Mechanical Systems; Jan. 22-24, 2002; p. 77-80.

Official Communication issued in corresponding Japanese Patent Application No. 2008-533941, mailed on Sep. 7, 2010.

* cited by examiner

APPARATUS AND METHOD FOR DETERMINING THE VOLUME FRACTIONS OF THE PHASES IN A SUSPENSION

TECHNICAL FIELD

The present application relates to an apparatus and a method for determining the volume fractions of the phases in a suspension, i.e. a multi-phase mixture containing a liquid phase and a solid phase. In particular, the present invention is suited for determining the hematocrit value HKT of whole blood, i.e. the ratio of the partial volume of the cellular constituents to the overall volume.

BACKGROUND

Methods for determining the hematocrit value HKT of blood are known. One known method for determining the hematocrit value is based on an electrical conductance measurement, wherein the measured conductance is inversely proportional to the hematocrit. Such methods are described, for example, in "Labor und Diagnose" by Lothar Thomas, TH-Books, 5$^{th}$ volume, 1998, and K. Dörner, "Klinische Chemie und Hämatologie", Georg Thieme Verlag, Stuttgart, Germany, 1998, 2003. Moreover, products for hematocrit determination using electrical conductance measurement were offered by iSTAT Corporation, East Windsor, N.J., USA (http://www.istat.com) at the time of application.

A further method for determining the hematocrit value is referred to as micro-hematocrit method. Here, a micro-capillary having an internal diameter of 1 mm is dipped into the blood to be measured. The blood rises in the capillary, driven by the capillary force. This is now sealed at one end and inserted into a micro-hematocrit centrifuge or a microhematocrit rotor, and centrifuged according to the NCCLS standard. The determination of the hematocrit value HKT takes place either by a measurement disk or a measurement assembly. Direct readout of the hematocrit value is possible still in the centrifuge with the measurement disk. The great disadvantage of this method is the necessary manual sealing of the capillary.

The micro-hematocrit method is approved as a reference method, wherein the values obtained are up to about 2% higher than the comparative measurements with a hematology analyzer, due to the enclosed plasma. With respect to this micro-hematocrit method, for example, reference may be made to K. Dörner, Klinische Chemie und Hämatologie, Georg Thieme Verlag, Stuttgart, Germany, 1998, 2003, or B. Bull et al., Pennsylvania, USA, ISBN 1-56238-413-9 (1994). Furthermore, this technology is practiced by the company Hermle Labortechnik GmbH at the time of application (http://www.hermle-labortechnik.de).

Methods for filling blind channels, i.e. channels with one closed end, which are supposed to prevent enclosure of bubbles, are known. Such methods are described, for example, in Steinert C P Sandmeier H, Daub M., de Heij B., Zengerle R. (2004), Bubble free priming of blind channels, in Proceedings of IEEE-MEMS, Jan. 25-29, 2004, Maastricht, The Netherlands, p. 224-228; and Goldschmidtboeing F., Woias P. (2005), Strategies for Void-free Liquid-filling of Micro Cavities, in Proceedings of Transducers '05 Conference, June 5-9, Seoul, Korea, ISBN 07-7803-8994-8, p. 1561-1564; as well as in DE 10325110 B3.

SUMMARY

According to an embodiment, an apparatus for determining the volume fractions of the phases in a suspension may have: a body; a channel structure, which is formed in the body and has an inlet area and a blind channel, which is fluidically connected to and capable of being filled via the inlet area; and a drive for imparting the body with rotation, so that phase separation of the suspension in the blind channel takes place by centrifugation, wherein the blind channel has such a channel cross-section and/or such wetting properties that, when filling same with the suspension via the inlet area, higher capillary forces act in a first cross-sectional area than in a second cross-sectional area, so that at first the first cross-sectional area fills in the direction from the inlet area toward the blind end of the blind channel and then the second cross-sectional area fills in the direction from the blind end toward the inlet area.

According to another embodiment, a method for determining the volume fractions of the phases in a suspension may have the steps of: providing a channel structure, which has an inlet area and a blind channel, which borders on the inlet area; introducing the suspension into the inlet area, wherein the blind channel has such a channel cross-section and/or such wetting properties that higher capillary forces act in a first cross-sectional area than in a second cross-sectional area, so that at first the first cross-sectional area fills in the direction from the inlet area toward the blind end and then the second cross-sectional area fills in the direction from the blind end toward the inlet area; and imparting the channel structure with rotation, to cause phase separation of the suspension in the blind channel by centrifugation.

The present invention relates to a novel concept to determine the volume fractions of the phases in a multi-phase mixture. The inventive concept here uses the effect of sedimentation in a blind channel if the same is subjected to centrifugation. The blind channel, according to the invention, includes such a channel cross-section and/or such wetting properties that an asymmetric capillary force occurs along the walls of the blind channel, which results in capillary filling of the channel advantageously in the area of the high capillary forces. Thereby, air is displaced into the area of the low capillary force, and furthermore in the direction of the inlet. Thus, by a quick filling rate in the area of the high capillary forces, the associated cross-sectional area of the channel is quickly filled in the direction from the open side toward the closed side, whereupon the areas with the low capillary force are filled in the direction from the blind end toward the inlet. This allows for filling the blind channel substantially without air enclosure. The blind channel thus can be filled with the sample with defined and usually infinitesimal bubble enclosure due to the channel cross-section and/or the wetting properties. The blind channel is subjected to centrifugation, so that phase separation of the suspension takes place and the particles are sedimented out of the suspension.

In embodiments, the channel structure may comprise an integrated overflow structure between inlet and blind channel for integrated volume definition of the sample. In further embodiments, a scale for reading the volume fractions may be integrated in the body in which the channel structure is formed. The body in which the channel structure is formed may be formed, in embodiments of the present invention, by a first layer, in which the channel structure is formed, and a second layer, which forms a lid.

So as to cause asymmetric capillary forces along the walls of the blind channel, the blind channel may comprise walls bordering on each other at different enclosed angles. Additionally or alternatively, the walls may be differently hydrophilic with respect to the suspension or comprise portions being differently hydrophilic with respect to the suspension. Again alternatively or additionally, the blind channel may comprise a cross-section with at least one step, so that a capillary force distribution having areas with higher capillary force and areas with lower capillary force results across the cross-section of the blind channel.

In the inventive method for determining the volume fractions of the phases in a suspension, the centrifugal force may further be used to effect accelerated filling of the blind channel. To this end, rotation of the channel structure may already be caused before the blind channel is completely filled.

The present invention allows for complete integration of all procedural steps necessary for hematocrit value determination, particularly with no later sealing of a capillary being necessary. Furthermore, the inventive apparatus may be produced via a simple process, since the body may simply consist of two layers, with the channel structure being structured in one thereof, whereas the other serves as a lid. Alternatively, both layers may be structured to define parts of the channel structure.

The present invention may be implemented as a so-called "lab-on-a-disk" system, wherein further medical tests may be integrated on the body, also taking advantage of centrifugal and capillary forces as well as further forces usual in so-called lab-on-a-chip systems. The present invention is particularly suited for determining the hematocrit value of blood, wherein the dimensions of the channel structure are adapted correspondingly, to be able to effect sedimentation of the blood into erythrocytes and plasma in the blind channel. Lab-on-a-chip systems are described, for example, in A. van den Berg, E. Oosterbroek, Amsterdam, NL, ISBN 0-444-51100-8 (2003).

The blind channel is designed for capillary filling with the suspension the volume fractions of which are to be determined, wherein filling thus may take place without centrifugal force. The centrifugal force may, however, be used supportively to accelerate the filling process by imparting the channel structure with rotation during filling.

BRIEF DESCRIPTION OF THE DRAWINGS

Embodiments of the present invention will be detailed subsequently referring to the appended drawings, in which.

DETAILED DESCRIPTION

The present invention is generally suited for determining the volume fractions of the phases in a multi-phase mixture, and is particularly applicable in advantageous manner for determining the hematocrit value of blood.

Substantially, the present invention includes a body and a drive means for imparting the body with rotation. The body may for example comprise a lidded substrate, in which channel structures are implemented, and may be set to rotation via a rotation motor. Here, the body may either itself be formed as a rotation body, for example a disk, which is placed onto a suitable coupling of the rotation motor, or the body may be formed as a module insertable into a rotor, which can be driven by a rotation motor. What is important for technical realization rather is the balance of the rotor than the exact shape of the body.

Figure 1:
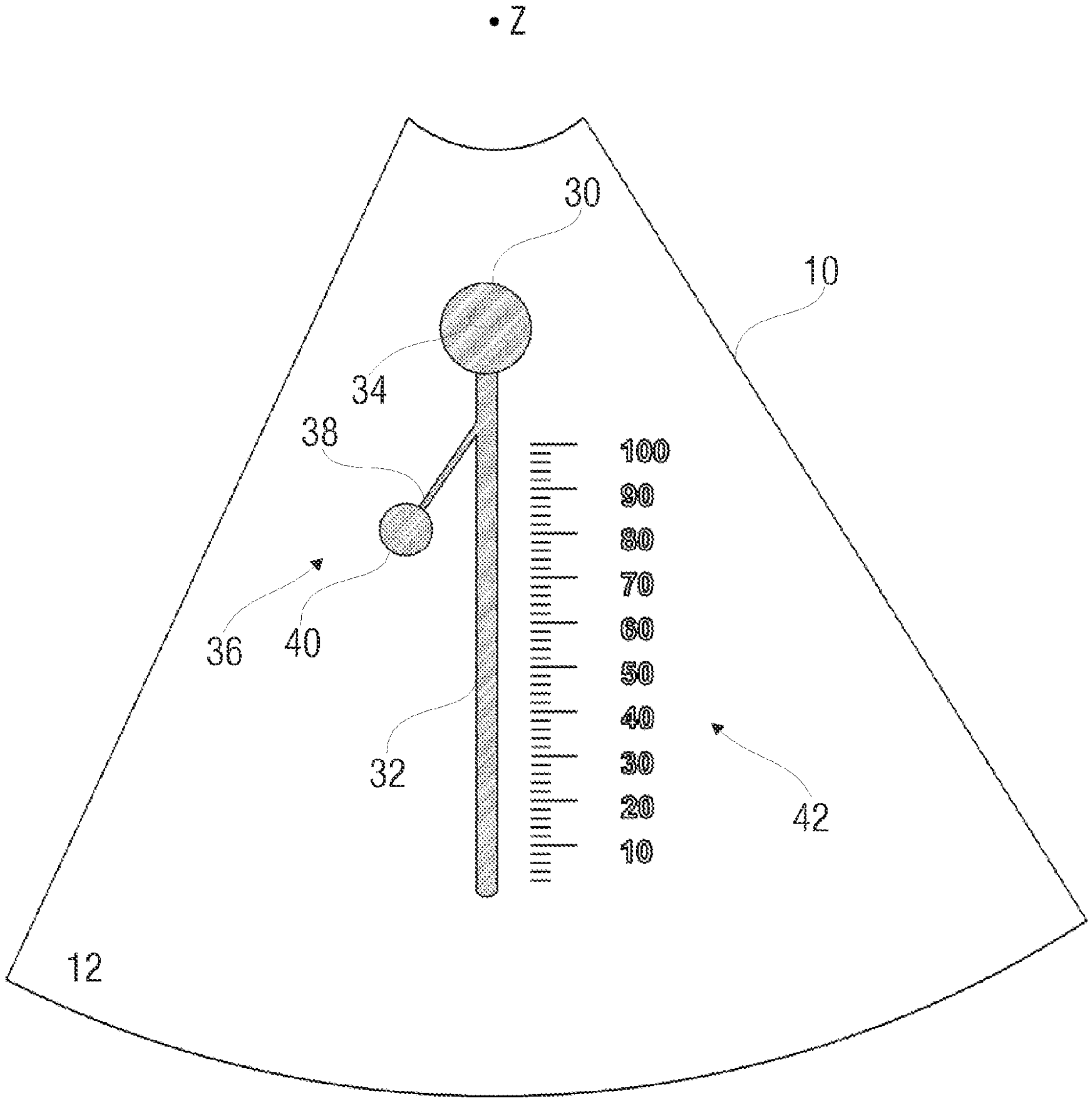
FIG. 1 is a schematic illustration of a substrate according to an embodiment of the invention.
Figure 10A:
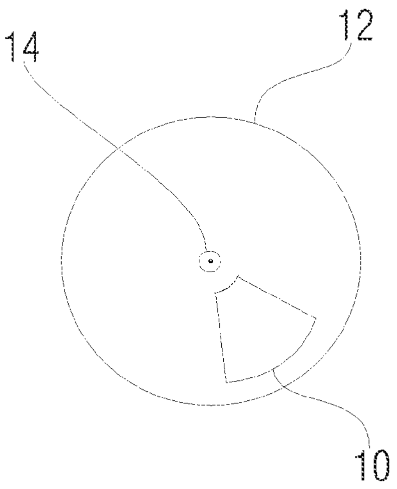
FIGS. 10A and 10B are schematic top views of embodiments of a substrate formed as a disk.
Figure 10B:
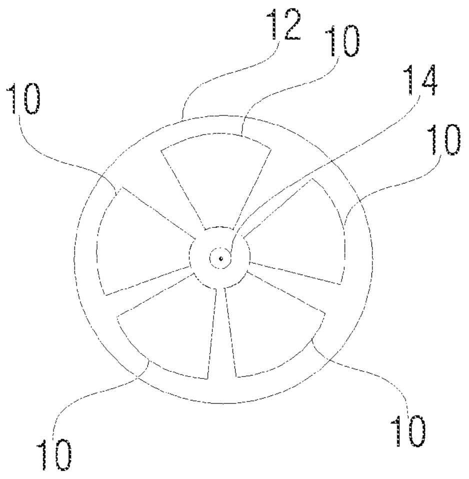

FIG. 1 shows a schematic top view onto an excerpt 10 of a substrate, which may for example be implemented as a disk 12, as it is shown in FIG. 10A. The substrate 12 may be constructed according to a conventional CD type, having a center opening 14, by means of which it may for example be attached at a conventional centrifuge. An alternative embodiment of a substrate 12', in which a plurality of channel structures are formed, which hence has a plurality of areas 10, is shown in FIG. 10B. By the substrate shown in FIG. 10B, in which five channel structures are formed, the hematocrit value of five blood samples can be determined concurrently or also successively.

Figure 11:
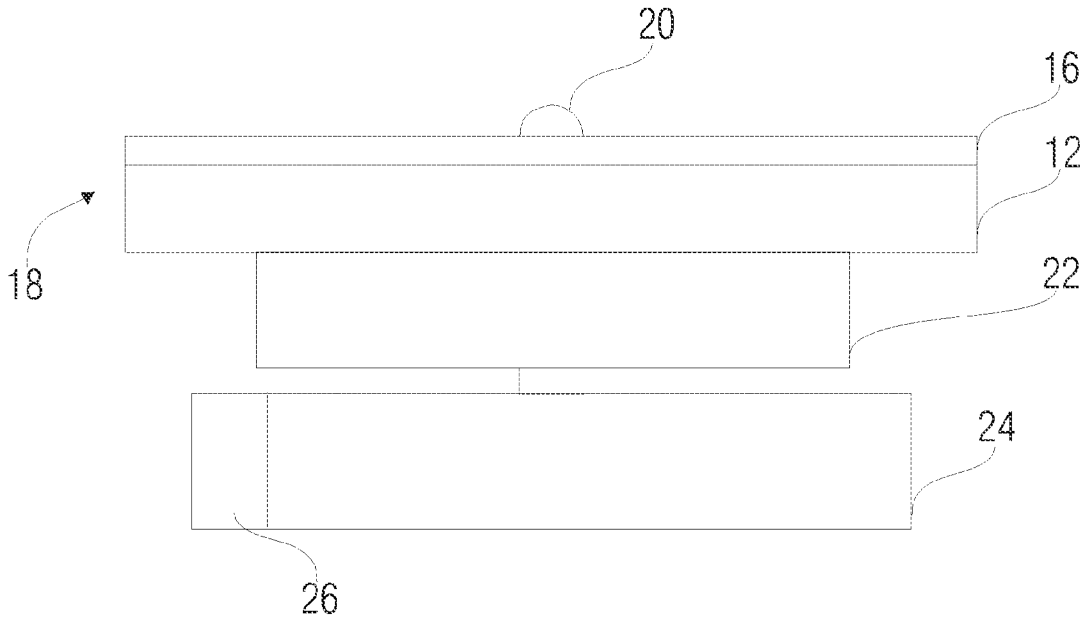
FIG. 11 is a schematic side view of an embodiment of an inventive apparatus.

As can be taken from FIG. 11, the substrate 12, in which the channel structures are formed, are provided with a lid 16. The substrate 12 and the lid 16 form a module body 18. The module body 18 is attached via a mounting means 20 to a rotating part 22 of a driving device, which is pivoted on a stationary part 24 of the driving device. The driving device may for example be a conventional centrifuge with adjustable rotational speed or also a CD or DVD drive. The driving device 24 includes a control means 26 to cause the respective rotations of the substrate 12 to perform the method according to the invention.

As shown in FIG. 1, a channel structure in the substrate comprises an inlet area 30 for the medium to be examined, which borders on a blind channel. The substrate 12 is rotatable about a rotation axis Z, so that the inlet area terminates radially outwardly into the blind channel 32. In the inlet area, for example, there is a hole 34 in the lid of the substrate, as indicated by dashed lines in FIG. 1. A sample may be introduced into the inlet area through the hole.

The channel structure includes, in the example shown, also an overflow structure 36, which comprises an overflow channel 38 and an overflow chamber 40, into which the overflow channel 38 leads. The overflow structure 36 serves for volume dosage of the sample, i.e. of the suspension. The overflow channel 38 of the overflow structure may represent a hydrophobic barrier for the dosage, which is overcome after the filling of the blind channel 32, so that a defined volume of the suspension is in the blind channel 32.

In the embodiment shown, the substrate 12 further includes a scale 42, which may for example be formed on or in the lid or on the upper side of the carrier layer 16. The scale 42 allows for direct optical readout of the volume of the phase fraction following the sedimentation.

The blind channel 32 is formed such that different capillary forces act in different cross-sectional areas thereof. In particular, the blind channel may be formed to obtain differently strong capillary forces along the edges of the channel. To this end, an angle of inclination of the sidewalls of the channel with respect to a perpendicular to the main surfaces of the substrate and/or the contact angle of the inner channel wall with the suspension to be sedimented can be adapted. In particular, zones with increased capillary pressure may be generated thereby, wherein the expansion of the menisci at the greatest speed then is along the zones with the increased capillary pressure.

Figure 2:
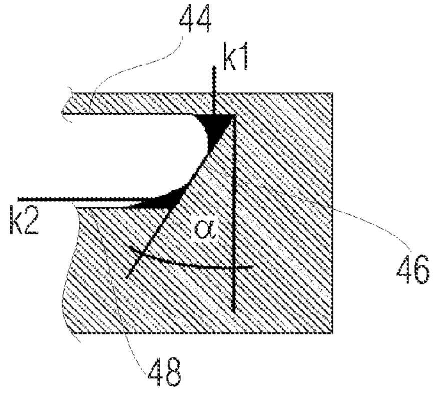
FIG. 2 is a schematic cross-sectional illustration of a channel for explaining an asymmetric capillary pressure distribution.

According to a first alternative, as it is schematically shown in FIG. 2, the walls of the blind channel and/or the walls of the entire channel structure (inlet and blind channel) may be inclined by an angle α. By such an inclination α, a differently high capillary pressure at edges k1 and k2 of the channel results, wherein a sidewall 46 and an upper wall 44 border on each other with a smaller enclosed angle at the edge k1 than the sidewall 46 with a channel bottom wall 48 at the edge k2. Thus, there is a higher capillary force in the area of the edge k1 than in the area of the edge k2. The area adjacent to the edge k1 thus represents an area of a higher capillary force, at which propagation of the meniscus of a suspension with which the channel is to be filled takes place at increased speed. Thus, it can be achieved that filling at first takes place in these areas in the direction from the inlet area toward the blind end, and the remaining areas then fill in the direction from the blind end toward the inlet area.

Figure 3:
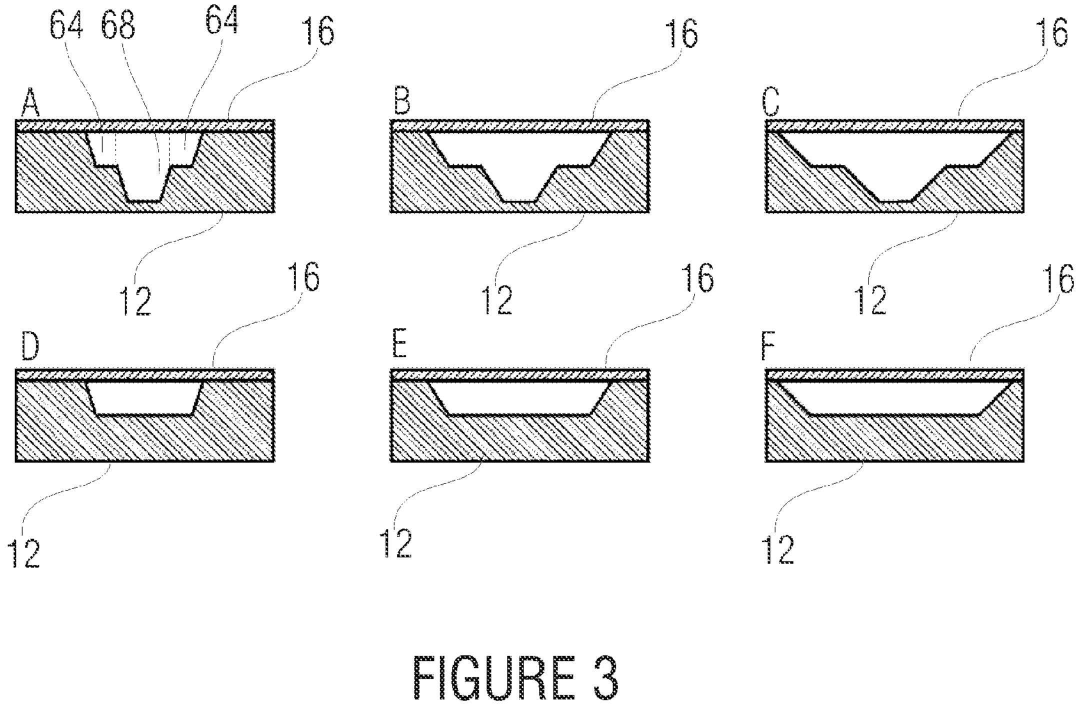
FIGS. 3A to 3F schematically show channel cross-sections, as may be used in embodiments of the invention.

Variations of channel cross-sections are shown in FIGS. 3A-3F, wherein the channel each is formed in the substrate 12, which is provided with a lid 16. In FIGS. 3A-3C, T channel cross-sections are shown, the sidewalls of which exhibit increasingly greater angles of inclination from FIG. 3A to 3C. An increased angle of inclination α of one and/or more channel walls increases the asymmetry of the capillary pressure.

In FIGS. 3D-3F, trapezoidal channel cross-sections are shown, the sidewalls of which have increasingly higher angles of inclination from FIG. 3D-3F, and hence increasingly higher asymmetry of the capillary force.

The channel cross-sections shown in FIGS. 3A-3C here represent an embodiment, since they allow for more reliable bubble-free filling. The described cross-sections are advantageous in that they can be produced in technically simple manner by usual milling tools.

Alternatively to the "oblique" T shapes shown in FIGS. 3A-3C, the channel cross-section could also have a T shape with substantially straight side faces, so that the channel has steps defining cross-sectional areas in which there are different capillary forces, so that substantially bubbly-free filling is possible thereby.

Figure 4:
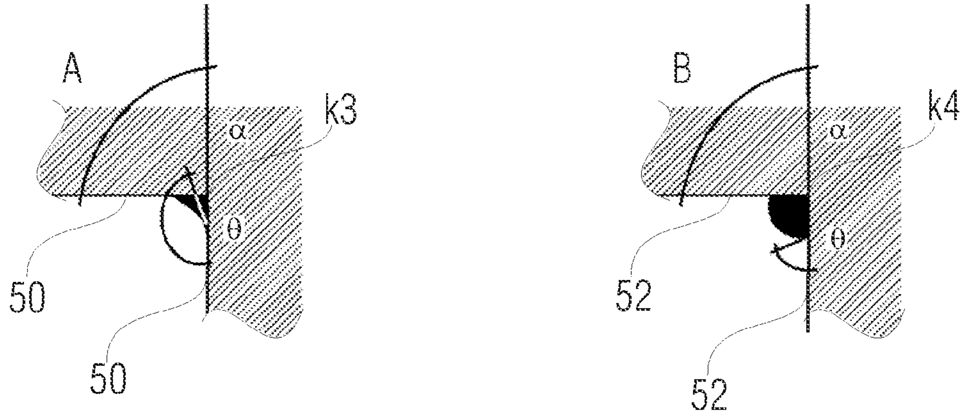
FIGS. 4A and 4B schematically show a respective portion of a channel cross-section for explaining the generation of an asymmetric channel pressure using different wetting angles.

As a further alternative, differently strong capillary pressures in the channel edges can be realized by variation of the contact angle θ. In this respect, FIG. 4A schematically shows an edge k3 of a channel the channel walls of which are made hydrophilic with respect to the suspension to be filled, such that a great contact angle θ is present. Thereby, a high capillary force results in the area of the edge k3. In contrast thereto, the channel walls at the edge k4 shown in FIG. 4B are made hydrophilic with respect to the suspension to be filled, such that a small contact angle θ results. Thereby, there is a smaller contact angle in the area of the edge k4.

According to FIGS. 4A and 4B, bubble-free filling of the hydrophilic blind channel thus may also take place based on the advantageous capillary filling along a certain part of the channel wall by variation of the contact angle θ, wherein the case shown in FIG. 4A provides a capillary filling favored in comparison with the case shown in FIG. 4B. An increased angle of inclination α of the channel wall may additionally increase the asymmetry of the capillary force. For example, it is possible to make the inside of the lid 16 more strongly hydrophilic than the walls of the substrate 12, so that a capillary force occurring on the edges between the lid 16 and the substrate 12 is increased as opposed to a capillary force occurring in an area on the edges between the sidewalls and the channel bottom. Furthermore, wall sections of individual walls may be made more strongly hydrophilic than others so as to there create areas at which a higher capillary force occurs than in other areas, so as to obtain the functionality described.

In summary, it can be stated that the capillary force in different cross-sectional areas of the blind channel is determined by the geometrical angles and the wetting angles, so that the effect of the blind channel at first being filled in the direction from the open end toward the blind end in certain areas and the remaining areas then being filled in the direction from the blind or closed end toward the open end can be achieved by a corresponding configuration of the channel cross-section using acute angles or sufficient hydrophylization. In other words, filling with a fast filling rate takes place in the areas with increased capillary force, whereas filling with a slow filling rate takes place in the areas with a low capillary force.

With respect to the theory of such a bubble-free filling capability of blind channels and/or their design, reference is made to the documents cited above, the disclosures of which in this respect are incorporated by reference.

Figure 5:
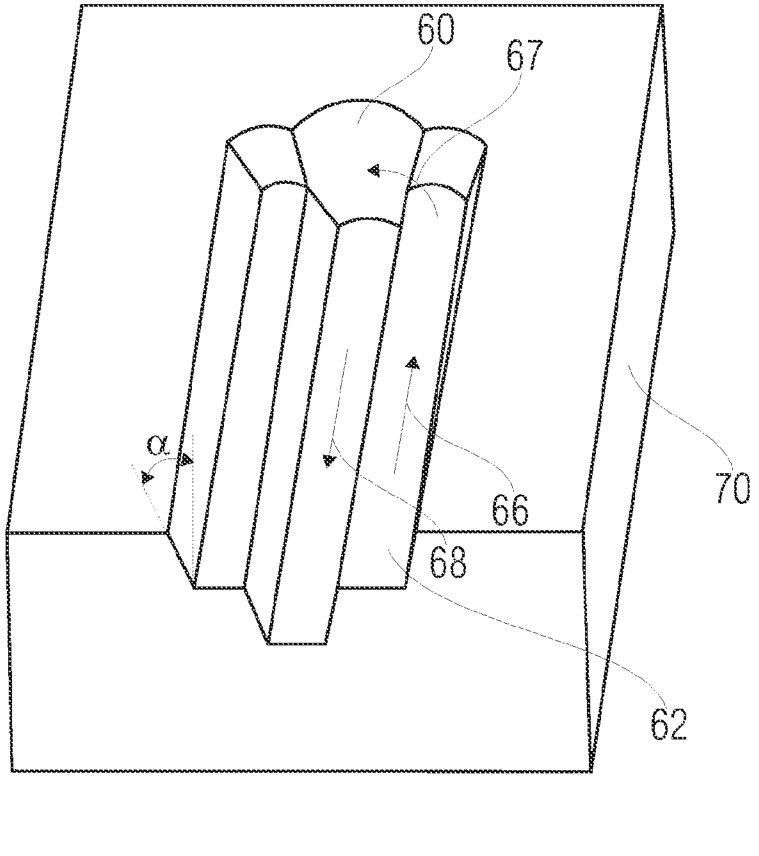
FIG. 5 is a schematic perspective view of the blind end of an embodiment of a blind channel the cross-section of which is shown in FIG. 3A.

A perspective view of a channel structure having a channel cross-section substantially corresponding to the cross-section shown in FIG. 3A is shown in FIG. 5. The channel cross-section has a T shape, the sidewalls of which have an angle of inclination α of about 17.5°. At the closed end 60 of the blind channel, which is generally designated with the reference numeral 62, there is a transition area. In the channel structure shown in FIG. 5, the outer areas of the crossbeam of the T structure, which are schematically marked in FIG. 3A and designated with the reference numeral 64, represent areas with increased capillary pressure. Thus, filling takes place from the open side of the blind channel 62 along these areas toward the closed end, as shown by an arrow 66 in FIG. 5. At the closed end 60, there is provided a transition so as to assist transition of the suspension into the inner area not yet filled, which is designated with the reference numeral 68 in FIG. 3A. This is indicated by an arrow 67 in FIG. 5. Subsequently, the blind channel fills further in the direction from the blind end 60 toward the open end, as indicated by an arrow 68 in FIG. 5.

In the case of a purely capillary filling, the transition area 62 is formed such that the capillary flow is not interrupted there. An important measure to this end, for example, is the avoidance of sharp transition edges. If this final phase of the capillary filling is assisted by centrifugation, geometries that can be filled not solely in capillary manner are also tolerable in the area 62, without putting the overall functionality of the blind-channel-based hematocrit determination at risk.

Channel structures, for example such as it is shown in FIG. 5, may for example be produced using a CNC (computer numerically controlled) micro-material treatment in a COC (cyclic olefin copolymer) disk using a tapering tool, yielding walls having an inclination of 17.5°. The upper and the lower plane of the two-plane capillary structure shown in FIG. 5 may for example have a depth of 400 μm, widths of 1400 μm and 400 μm, respectively, and radial lengths of 25 mm and 25.4 mm, respectively, with a transition at the closed end 60, as explained above.

The inner channel walls are made hydrophilic with respect to the suspension to be examined after producing the channel, due to the substrate material used, or are made hydrophilic correspondingly after producing the channel structures.

A sequence representing the filling of a blind channel, as it is shown in FIGS. 3A and 5, is shown in FIGS. 6A-6F, wherein 6A-6C show lateral longitudinal cross-sectional views, whereas FIGS. 6D-6F illustrate top views onto the channel structure shown in FIG. 5. The filling illustrated takes place without centrifugal force assistance, wherein a time axis at the left edge of FIGS. 6A to 6C indicates that the filling process up to the degree of filling shown in FIGS. 6C and 6F takes about 30 seconds.

Figure 6:
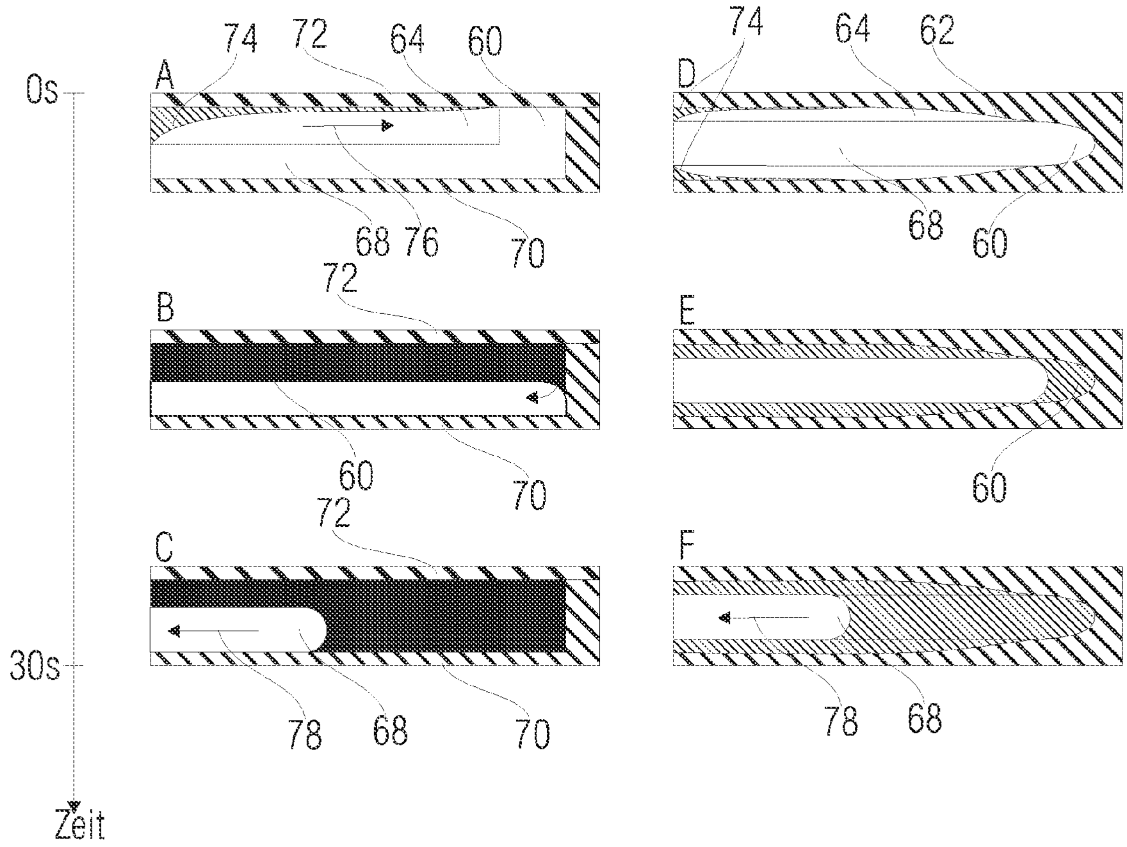
FIGS. 6A to 6C are side views of the channel shown in FIG. 5 in different phases of the filling thereof.
FIGS. 6D to 6F are top views of the channel of FIG. 5, also in different phases of filling thereof, corresponding to the phases of FIGS. 6A to 6C.

As can be seen in FIG. 6, the blind channel 62 is structured into a substrate 70 and closed by means of a lid 72. As explained with reference to FIGS. 4A and 5, the channel possesses areas 64 in which there is increased capillary force and areas 68 in which there is lower capillary force.

Upon introducing a suspension into an inlet area (not shown in FIGS. 6A-6F), which is fluidically connected to the blind channel 62 at the open end, the suspension is drawn along the critical edges between the inclined sidewalls and the lid by the capillary force, as shown by the suspension areas 74 in FIGS. 6A and 6D and indicated by the arrow 76 in FIG. 6A. After filling the areas 64 in the direction from the open end toward the closed end of the blind channel 62, the special shape of the closed end assists a seamless transition of the suspension into the area 68 along the edges, as can be seen in FIGS. 6B and 6E. This transition into the area 68 is further supported by the fact that the edges at the closed end of the blind capillaries are rounded. Then, filling of the still unfilled area 68 in the direction from the closed end 60 of the blind channel 62 toward the open end thereof takes place. This leads to complete evacuation of the channel, so that this has substantially been filled completely by the suspension without bubble inclusion.

Execution of an example of an inventive method using a channel structure having a channel 62, as it was described above, is shown in FIGS. 7A-7C. The channel structure includes the blind channel 62, an inlet area 80, as well as an overflow structure 82. The channel structures mentioned may again be formed in a substrate and covered by a lid, which may again comprise an opening 84 for introducing a suspension into the inlet area 80, which may represent an inlet reservoir.

Figure 7:
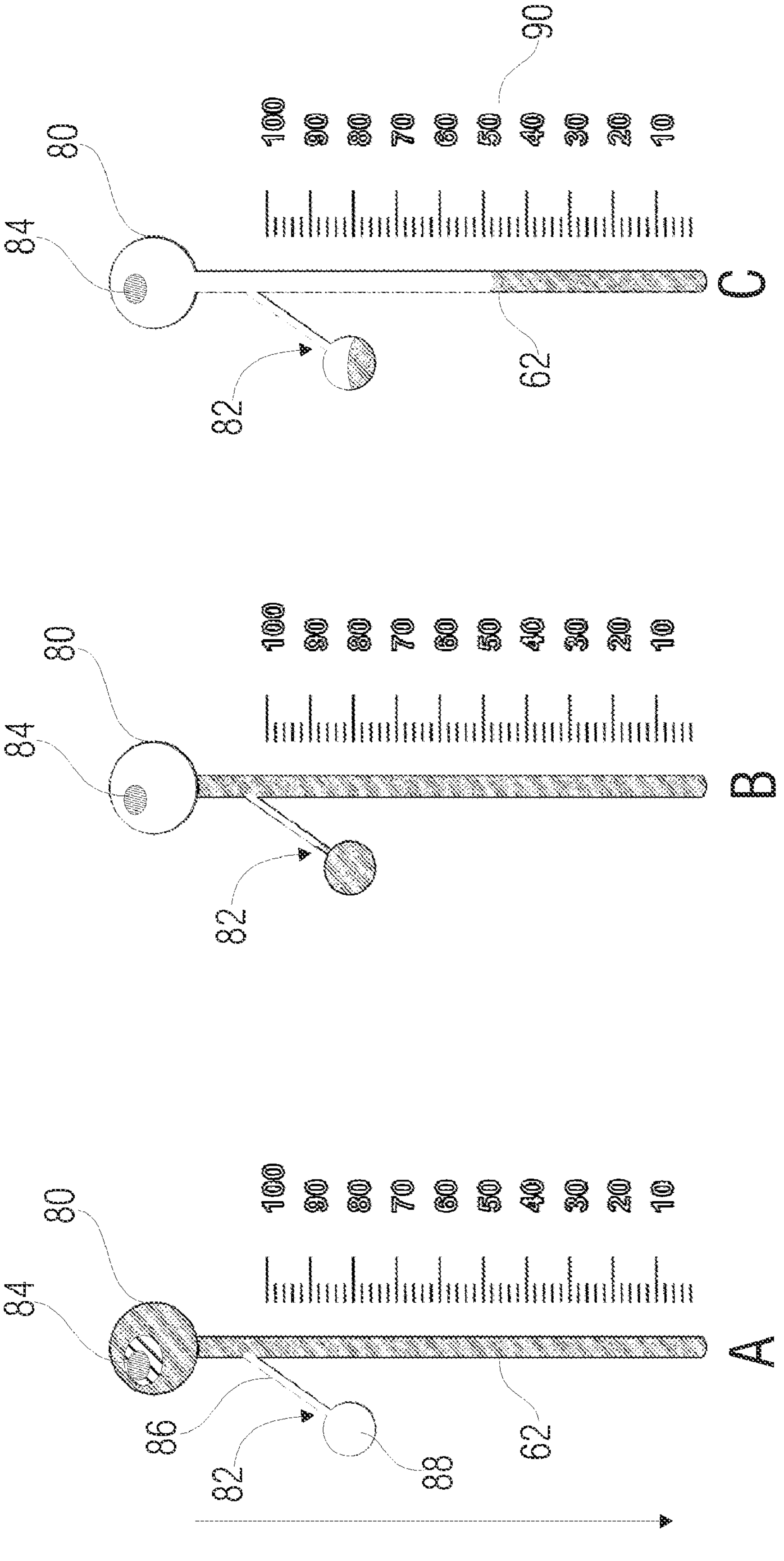
FIGS. 7A to 7C show a channel structure at different times of an embodiment of the inventive method.

In FIG. 7A, there is shown the state in which the blind channel 62 is completely filled with the suspension to be sedimented. After this filling, the rotational frequency is increased over the breakthrough frequency of an overflow channel 86 of the overflow structure 82, which is made hydrophobic at the entry, so that the excess suspension is drawn off into the overflow reservoir 88 via the overflow channel 86. FIG. 7B shows the channel structure after dosing off the excess suspension using the overflow structure 82. The limiting frequency for the breakthrough may for example be 30 Hz, wherein the suspension volume in the blind capillary 62 may for example be 20 μl. Then, the substrate in which the channel structure is formed is further subjected to rotation, for example at 100 Hz for five minutes, so that the suspension in the blind channel 62 is sedimented. FIG. 7C shows the channel structure after sedimentation. The volume fraction of the deposited sediment and/or the hematocrit value may then be determined at rest via the ratio of the radial position of the liquid-solid interface and the known length of the capillary. Advantageously, a scale 90 located on the substrate may be used for reading the hematocrit value.

Figure 8:
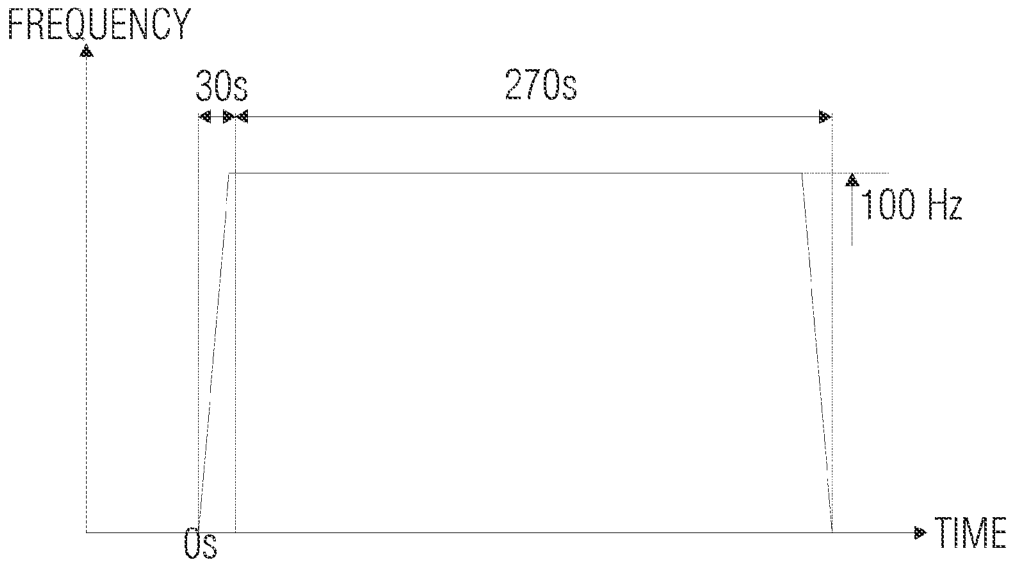
FIG. 8 is a frequency protocol for control of a drive means during the execution of an embodiment of the inventive method.

FIG. 8 shows a possible frequency protocol for operating the driving device, for example the rotation motor. At the beginning, the rotational frequency is increased to 100 Hz, for example, wherein the centrifugal force generated hereby may assist the filling process. After exceeding the limiting frequency of the overflow structure, the excess suspension flows into the suspension reservoir 88. So as to cause sedimentation of the suspension in the blind channel, rotation at a substantially constant rotational speed takes place, whereupon the rotation is terminated by breaking over a certain time interval. After the standstill, the volume fraction can be read using the scale by an operator or automatically via an optical detection means.

Figure 9:
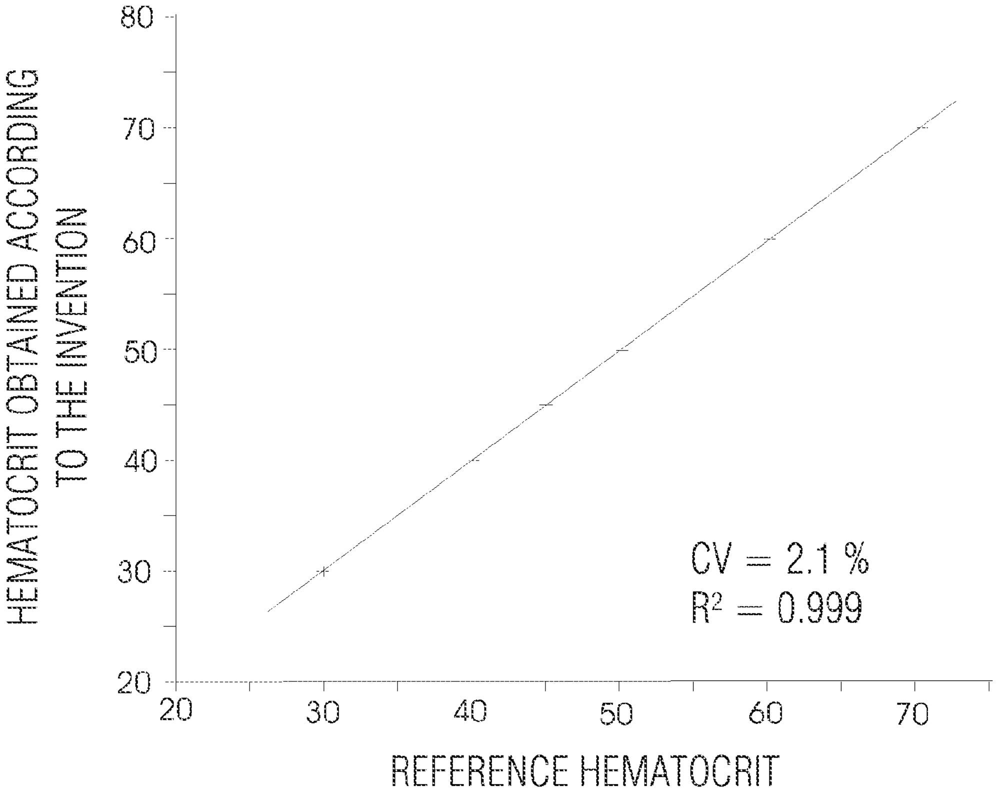
FIG. 9 schematically shows the result of a measurement series for hematocrit determination using a channel structure, as it is shown in FIG. 7.

FIG. 9 shows the result of a measurement series for determining the hematocrit value, which was obtained using the above-described apparatus and with the described method. The reference determination here takes place with the aid of a micro-hematocrit rotor Z 233 M-2 of the company Hermle Labortechnik in a centrifuge by the same company.

FIG. 9 shows that a CV value of 2.1% and high linearity between the inventively obtained hematocrit value and the reference measurement, $R^2=0.999$, was obtained in a determination time of five to six minutes.

Hence, the present invention provides a novel concept suited for determining a centrifuge-based hematocrit test in a blind capillary. The test may be implemented by a frequency protocol on a simple two-plane structure, which may easily be achieved using inexpensive mass production, for example injection molding. The test is very exact and necessitates a blood volume of only 20 μl. Moreover, readout by visual inspection on a printed scale eliminates the need for expensive detection equipment, wherein the hematocrit test could in principle be run on a conventional CD drive. So as to achieve rotational symmetry of the disk, it may further be advantageous to implement parallelization of channels, as it was explained above with reference to FIG. 10B, which is of particularly advantage for routine blood separation.

In embodiments of the present invention, there may further be provided a possibility to allow for readout during or after the rotation. To this end, a suitable measurement instrument may be provided. This may for example comprise a photo camera with short aperture time or a stroboscopic camera, to detect the blind channel, with an associated scale if necessary. The measurement instrument may further comprise an evaluation means to evaluate the captured images and determine the hematocrit value therefrom.

The substrate in which the channel structures are formed may be formed of any suitable materials, for example plastics, silicon, metal or the like. Furthermore, the substrate and the structures formed therein may be produced by suitable manufacturing methods, for example micro-structuring or injection molding techniques. The lid of the inventive substrate may consist of a suitable, advantageously transparent material, for example glass of pyrex glass.

With reference to the embodiments, the body of substrate and lid has been described as a rotation body with a rotation axis, wherein the drive means is formed to rotate the rotation body about its rotation axis. Alternatively, the body may have a substantially arbitrary shape, wherein the drive means comprises a fixture for holding the body and for rotating the substrate about a rotation axis lying outside the substrate.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for determining the volume fractions of the phases in a suspension, comprising:
- a body;
- a channel structure, which is formed in the body and comprises an inlet area and a blind channel, which is fluidically connected to and capable of being filled via the inlet area;
- a drive for imparting the body with rotation, so that phase separation of the suspension in the blind channel takes place by centrifugation; and
- a controller to control the drive, wherein
- the blind channel comprises such a channel cross-section and/or such wetting properties that, when filling same with the suspension via the inlet area, higher capillary forces act in a first cross-sectional area than in a second cross-sectional area, so that at first the first cross-sectional area fills in the direction from the inlet area toward a blind end of the blind channel by capillary force and then the second cross-sectional area fills in the direction from the blind end toward the inlet area by capillary force,
- the channel structure further comprises an overflow structure between the inlet area and the blind channel for volume dosage of the suspension, wherein the overflow structure comprises an overflow channel branching from the blind channel and extending in a partially radial direction to an overflow chamber, and
- the controller is configured to control the drive such that, upon completely filling the blind channel with the suspension by capillary force, the body is imparted with a rotational frequency that exceeds a breakthrough frequency of the overflow channel so that excess suspension is drawn off into the overflow chamber and a defined volume of the suspension is in the blind channel so that phase separation of the suspension in the blind channel takes place in the defined volume.

2. The apparatus according to claim 1, wherein the body comprises a scale, which is arranged relative to the blind channel such that the volume fraction in the blind channel can be read.

3. The apparatus according to claim 1, wherein the body comprises a first layer, in which the channel structure is formed, and a second layer, which forms a lid.

4. The apparatus according to claim 1, wherein the body is formed as a rotation body with a rotation axis, wherein the drive is formed to rotate the rotation body about its rotation axis.

5. The apparatus according to claim 1, wherein the drive comprises a fixture for holding the body and for rotating the body about a rotation axis lying outside the body.

6. The apparatus according to claim 1, wherein the blind channel comprises walls bordering on each other with different angles enclosed therebetween.

7. The apparatus according to claim 1, wherein the blind channel comprises walls, which are differently hydrophilic with respect to the suspension or which comprise portions being differently hydrophilic with respect to the suspension.

8. The apparatus according to claim 1, wherein the blind channel comprises a cross-section with at least one step.

9. The apparatus according to claim 1, wherein the blind channel comprises a T-shaped channel geometry.

10. The apparatus according to claim 1, wherein the blind channel comprises an upper wall and a lower wall and at least one sidewall arranged at an angle different from 90° with respect to the upper wall and the lower wall.

11. The apparatus according to claim 1, further comprising a determinator for determining the volume fractions in the blind channel during or after the rotation.

12. A method for determining the volume fractions of the phases in a suspension, comprising:
- providing a channel structure, which comprises an inlet area, a blind channel which borders on the inlet area, and an overflow structure between the inlet area and the blind channel for volume dosage of the suspension, wherein the overflow structure comprises an overflow channel branching from the blind channel and extending in a partially radial direction to an overflow chamber;
- introducing the suspension into the inlet area, wherein the blind channel comprises such a channel cross-section and/or such wetting properties that higher capillary forces act in a first cross-sectional area than in a second cross-sectional area, so that at first the first cross-sectional area fills in the direction from the inlet area toward a blind end of the blind channel by capillary force and then the second cross-sectional area fills in the direction from the blind end toward the inlet area by capillary force;
- upon completely filling the blind channel with the suspension by capillary force, imparting a rotational frequency to the channel structure that exceeds a breakthrough frequency of the overflow channel so that excess suspension is drawn off into the overflow chamber and a defined volume of the suspension is in the blind channel;
- imparting the channel structure with rotation, to cause phase separation of the defined volume of the suspension in the blind channel by centrifugation; and
- determining the volume fractions of the separated phases in the blind channel.

13. The method according to claim 12, wherein the channel structure is imparted with rotation prior to complete filling of the blind channel by capillary force, in order to accelerate the filling by taking advantage of centrifugal force.

14. The method according to claim 12, wherein the suspension is blood and wherein the dimensions of the channel structure are adapted to determine the hematocrit of blood.

15. The method according to claim 12, further comprising determining the volume fractions in the blind channel during or after the rotation.

* * * * *